United States Patent [19]
Pohndorf et al.

[11] Patent Number: 4,848,352
[45] Date of Patent: Jul. 18, 1989

[54] METHOD FOR CARDIAC PACING AND SENSING USING COMBINATION OF ELECTRODES

[75] Inventors: Peter J. Pohndorf, Raleigh, N.C.; Edward A. Schroeppel, Miramar, Fla.

[73] Assignee: Telectronics, N.V., Netherlands

[21] Appl. No.: 217,085

[22] Filed: Jul. 7, 1988

Related U.S. Application Data

[63] Continuation of Ser. No. 14,813, Feb. 13, 1987, abandoned.

[51] Int. Cl.⁴ .......................... A61B 5/04; A61N 1/05
[52] U.S. Cl. .................. 128/642; 128/419 P; 128/786
[58] Field of Search .............. 128/784–786, 128/419 P, 419 D, 642, 303.17

[56] References Cited

U.S. PATENT DOCUMENTS

| | | | |
|---|---|---|---|
| 3,825,015 | 7/1974 | Berbovits | 128/786 |
| 3,920,021 | 11/1975 | Hiltebrandt | 128/303.17 |
| 3,977,411 | 8/1976 | Hughes, Jr. et al. | 128/786 X |
| 4,289,134 | 9/1981 | Bernstein | 128/786 X |
| 4,379,462 | 4/1983 | Borkan et al. | 128/786 |
| 4,437,474 | 3/1984 | Peers-Trevarton | . |
| 4,444,195 | 4/1984 | Gold | 128/786 X |
| 4,458,695 | 7/1984 | Peers-Troverton | 128/786 |
| 4,579,119 | 4/1986 | Callaghan | . |
| 4,603,696 | 8/1986 | Cross, Jr. et al. | 128/419 P |
| 4,603,705 | 8/1986 | Spercher et al. | 128/786 |
| 4,630,611 | 12/1986 | King | 128/786 X |
| 4,674,518 | 6/1987 | Selo | 128/786 X |

OTHER PUBLICATIONS

Elecath Cardiovascular Catheters and Instruments, 1972, pp. 1-25.
CRC Critical Reviews in BioEngineering, dated 6/75 entitled The Current Status of Cardiac Pacing by O. Z. Roy, pp. 259-327.

*Primary Examiner*—Lee S. Cohen
*Attorney, Agent, or Firm*—Gerstman & Ellis, Ltd.

[57] ABSTRACT

A method for cardiac pacing and sensing is disclosed. A cardiac pacing lead is inserted into a heart chamber. The lead carries a plurality of separate electrodes positioned at the distal tip of the lead and transversely spaced from and electrically isolated from each other. A separate electrical conductor is provided for each electrode. A plurality of the electrodes are combined via electrical conductors to provide a relatively large electrode area for sensing cardiac activity. One of the electrodes is used for providing pacing pulses to the heart chamber. The pacing electrode has a relatively smaller surface area than the relatively large surface area used for sensing.

1 Claim, 1 Drawing Sheet

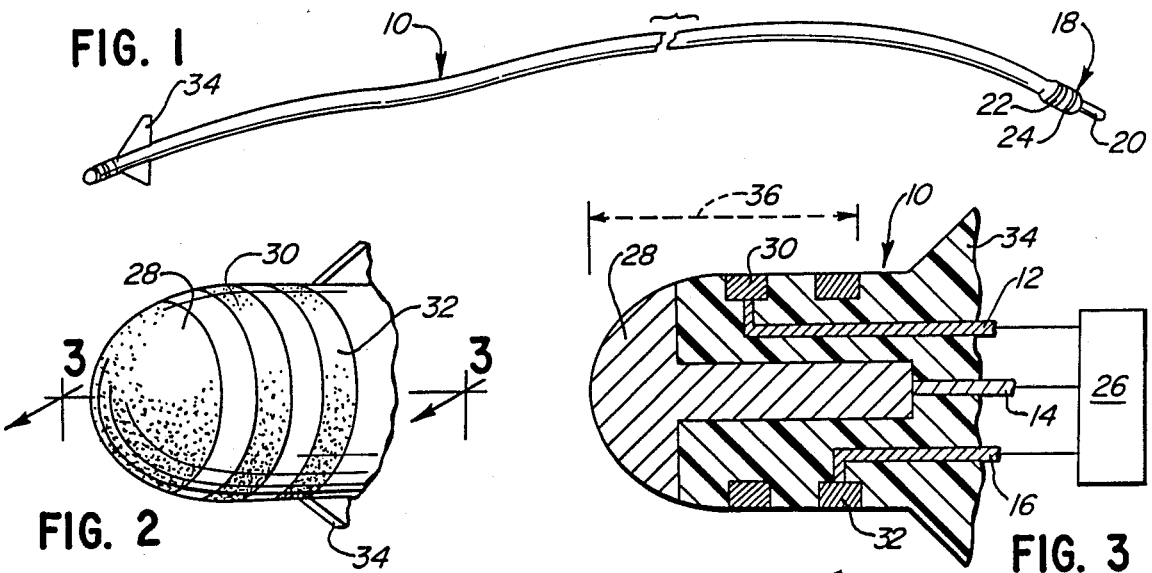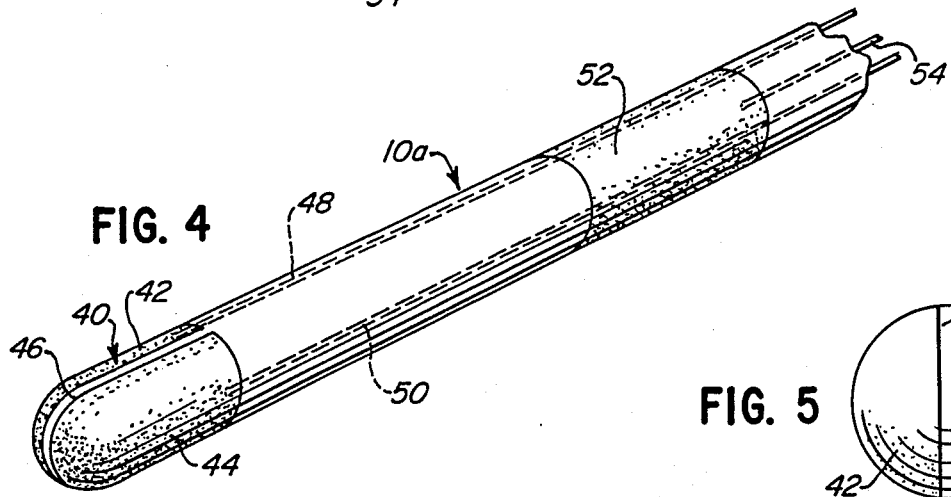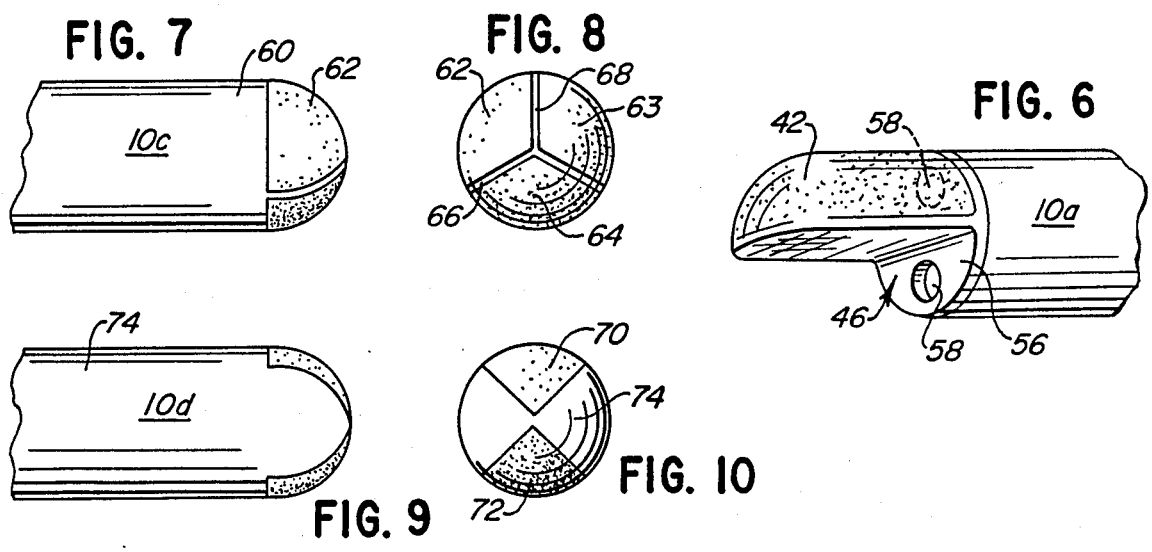

METHOD FOR CARDIAC PACING AND SENSING USING COMBINATION OF ELECTRODES

This application is a continuation of U.S. application Ser. No. 014,813, filed Feb. 13, 1987, now abandoned.

BACKGROUND OF THE INVENTION

Recent developments in the area of cardiac pacing have required the development of pervenous pacing leads with multiple electrodes. Usually such pervenous leads have a hemispherically shaped tip electrode and one or more ring electrodes spaced from the tip electrode and from each other. See for example Callaghan U.S. Pat. No. 4,579,119.

The electrodes of such leads are generally positioned on that portion of the lead which occupies the heart chambers. Pairs of electrodes may be interconnected and coupled to a conductive band in the terminal assembly of the pervenous lead adapted to be placed within the cardiac pacer. Alternatively, the tip electrode and each band electrode may be coupled to a separate conducter wire which is in electrical contact with a totally dedicated band electrode on the terminal assembly.

In "closed loop" pacing, where the parameters of the implanted cardiac pacer are modified in response to a sensed change, for example blood oxygen level, a sensing means is required. It has been suggested that the sensor use an electrode which is in contact with blood within the heart, as part of a detection system for oxygen, or another material, in the blood.

However, in the prior art, generally only one of the several electrodes is in a position where it can be in contact with the heart tissue at, for example, the site of pacing. Accordingly, pacing must take place at all times from the same electrode which, of course, has a constant size and most other common electrode characteristics. Accordingly, should requirements change in the pacing schedule or the like, the physician must either "make do" with the pacing electrode that he has in contact with the heart, or install another pacing lead in the patient, which is a significant surgical procedure. Additionally, if the lead wire to the pacing electrode breaks, or there is any other malfunction, in conventional leads pacing will immediately stop.

By this invention, an electrode of improved flexibility and redundancy of use is provided, in which more versatile procedures may be performed through the plural electrodes present on the lead, and in which a broken connector wire to one of the electrodes will not necessarily terminate operation of the lead.

DESCRIPTION OF THE INVENTION

The invention of this application relates to a lead, typically for medical purposes, which carries electrode means. The electrode means is subdivided into a plurality of separate electrode members which are located in a common, longitudinal area on the lead, i.e., the electrodes are in overlapping relation with respect to the longitudinal dimension of the lead. However, the electrodes are spaced from and electrically isolated from each other, with each electrode member being connected to a separate, electrically insulated conductor communicating along the lead.

The lead of this application may be connected to switching means, communicating with the conductors, for providing intermittent electrical connection between at least two of the separate electrode members for joint operation together.

It is also generally preferable for the electrode members to be made of substantially identical materials, to facilitate variations of polarity between them. As the result of this, a versatile, multiple electrode lead is provided in which versatile and variable usage may be made of the electrode members. Because of the independent leads provided to each electrode member, each electrode member may be electrically attached to a switching circuit as in a pacer, for example, for use in cardiac pacing. Thus, the individual electrode members may be switched on and off as desired in different combinations. For example, by this invention it becomes possible to change electrode size to optimize the threshold of sensing in one circumstance, and at another part of the cycle to reduce the electrode size by making use of only one of the electrode members for purposes of emitting a pulse for pacing or the like.

Thus, a large electrode surface may be provided for sensing, making use of a plurality or all of electrode members present, while pacing takes place from only one of the electrode members. Alternatively, one electrode member may be dedicated to pacing, and the other electrode members used for sensing. Additionally, different electrode members may be used for pacing at different times. Specifically, should one of the electrode members malfunction, another electrode members may be present and in a position to take up the pacing.

As a further alternative, upon installation of the lead into the heart, each of the separate electrode members may be tested for their suitability for pacing, which may vary with the particular position of the catheter, and the one most suited for pacing may be used. Likewise, in the event of malfunction, one of the electrode members may take over the function of another, failing electrode member.

Thus, by this invention, more than one electrode may be active at any given time and used for independent medical purposes, while another electrode on the same lead serves a different purpose.

In addition to the possibilities cited above, one or more of the electrode members may act as a sensor to detect changes in various parameters of the blood, for example, biochemical parameters. For example, blood oxygen or carbon dioxide levels may be measured by the use of an appropriate electrode as one of the electrode members at one point in a process, while acting as a sensor for electrical heart activity at another point in the process. Alternatively, a special electrode may be dedicated to such biochemical sensing.

The electrode members are preferably positioned at the distal end of the lead. One particularly useful configuration is to provide the electrode members as transversely separate insulated sections of an exposed tip on an end of the lead.

It is also preferable for the electrode members to occupy a length of said lead of no more than 0.5 cm., with spacings between the electrode members being preferably no more than 3 mm. The spacings between the electrode members must, of course, be sufficient to provide good electrical insulation between them, so that they do not directly influence each other by their respective operations, but can operate in an independent manner as governed by the pacer electronics or any other desired control system.

As a preferred design, the electrode members of this invention may reside on the distal end of a lead, with the exact tip of the lead defining a hemispherical electrode, and with spaced electrode rings being provided behind the tip, each being separated from the other electrode members and the whole system of electrode members all occupying a length of said lead of no more than 0.5 cm.

When the electrode members of this invention all occupy a length of no more than about 0.5 cm., they can all enter into electrical contact with heart tissue in such a manner as to individually and alternatively serve as a pacing electrode, which may be desired. Additionally, they may individually or collectively be used as a sensing electrode, as the needs may dictate, providing great and improved flexibility of use to medical leads, and particularly to pacing leads.

DESCRIPTION OF THE DRAWINGS

In the drawings, FIG. 1 is a perspective view of a heart pacing lead in accordance with this invention;

FIG. 2 is a fragmentary, enlarged perspective view of the distal end of the lead of FIG. 1;

FIG. 3 is a sectional view taken along line 3—3 of FIG. 2;

FIG. 4 is a fragmentary perspective view of the distal end of another embodiment of heart pacing lead in accordance with this invention;

FIG. 5 is an elevational view of the distal end of the pacing lead of FIG. 4;

FIG. 6 is a fragmentary perspective view, with a portion broken away, of the pacing lead of FIG. 4;

FIG. 7 is a fragmentary elevational view of the distal end of another embodiment of a heart pacing lead in accordance with this invention;

FIG. 8 is an elevational view of the distal end of the pacing lead of FIG. 7;

FIG. 9 is a fragmentary elevational view of the distal end of yet another embodiment of pacing lead in accordance with this invention; and FIG. 10 is an elevational view of the distal end of the pacing lead of FIG. 9.

DESCRIPTION OF SPECIFIC EMBODIMENTS

Referring to FIGS. 1 through 3, pacing lead 10 is provided, being of conventional design except as otherwise indicated herein. Lead 10 comprises three electrical connector wires 12, 14, 16 which extend the length of lead 10, being enclosed with insulating materials such as polyurethane, and communicating with terminal connector means 18 of conventional design at the proximal end of lead 10. One of the conductors 12 may communicate with pin 20, while the other conductors 14, 16 may communicate in conventional manner with terminal rings 22, 24 so that the respective conductors 12-16 may constitute separate insulated circuits from each other except when it is specifically desired to join them together into a single circuit. Electrical conductors 12 through 16 may therefore communicate through connector means 18 with appropriate pacer electronics 26, which may be of conventional design, modified to accomplish the particular purposes desired.

Conductors 12-16 communicate at their distal ends each with an electrode member. Electrode member 28 may be a hemispherical tip electrode as shown, while the remaining electrodes 30, 32 may be ring electrodes. Each conductor may be connected by appropriate soldering or brazing to an appropriate point on each electrode 28-32.

Additionally, lead 10 may carry wing members 34, or any other desired retention member, to retain the distal end of the lead in a desired position within or adjacent the heart to provide suitable contact of heart tissue with electrodes 28-32.

In accordance with this invention, the plurality of separate electrode members 28, 30, and 32 all occupy a length of said lead which is no more than 0.5 cm., as illustrated by line 36. Because of this, it becomes possible for each of the electrodes 28, 30, 32 to enter into electrically conductive relation with certain critical heart areas so as to permit pacing to take place from any or all of the electrodes 28-32, and also for sensing to take place from any or all of the electrodes. Thus, a greatly improved flexibility of use can be achieved by the electrodes of this invention, in which it may be possible for the heart to be paced with an electrical pulse emitted by any of the single electrodes 28, 30, or 32, while sensing, for example, may take place with the group of two or three of the above electrodes. This solves the long standing and known problem in which it is deemed preferable to emit a pacing pulse from a small electrode area, but to sense heart electrical activity from a large electrode area. By the invention of this application, such can be done, making use of appropriate and conventional switching in pacer electronics 26 during a pacing procedure which makes use of lead 10.

Additionally, one of electrodes 30 or 32, for example, may become a blood oxygen sensing electrode, or any other desired analytical device or a biophysical sensing electrode, e.g. to measure pressure, rather than an electrode which paces or senses heart electrical activity.

Further modifications of use of electrodes 28-32 may also be performed, with appropriate modifications taking place even after lead 10 has been installed into electrical communication with the heart of a patient, or any other medical use, by modification of the specific electronics and switching unit 26 as may be desired. Thus, upon a failure for any reason of electrode member 28 to provide effective pacing, the pacing function may be taken over by one of electrode members 30 or 32. Likewise, the area of sensing may be modified by applying any or all of electrode members 28-32 to the sensing function by appropriate modification of the switching and electronics of unit 26.

Referring to FIGS. 4 and 5, the distal end of a medical lead 10a is shown, which, except as otherwise indicated, may be identical in structure and function with lead 10. At the actual distal end of lead 10a is an end tip electrode portion 40, comprising a pair of electrode members 42, 44 which comprise transversely separate, insulated electrode sections, separated by a thin insulating member 46 of any desired plastic or ceramic insulating material. As shown, lead 10a carries internal conductors 48, 50 similar in function and structure to conductors 12-16 of the previous embodiment. Conductors 48-50 typically extend the length of lead 10a to a connector member at the proximal and thereof which may be similar in function to connector 18.

An optional, added ring electrode 52 may also be provided on lead 10a, or any of the leads shown herein, with electrode 52 being also connected to a conductor wire 54 for communication with a terminal pin or other connector similar to member 18. Unlike ring electrodes 30 and 32, electrode 52 is positioned a substantial distance away from electrode members 42, 44, in excess of 0.5 cm., for conventional use of a second ring electrode, as is well known in the technology of cardiac pacing leads.

As before, electrode members 42, 44 may be used together for a common purpose such as sensing, or they may be used separately for separate purposes as may be desired from time to time during a pacing program as determined by the electronics of the pacer. It can be seen that electrode members 42, 44, being located in a common longitudinal area on the lead, are uniquely available for versatile and variables uses. They may operate together as a single electrode, or they may be operated with separate functions, since they are electrically insulated from each other except by the conductive paths through conductors 48, 50 if so dictated by the electronic switching unit to which conductors 48, 50 are connected.

FIG. 6 shows the distal end of lead 10a in a partially disassembled configuration. Insulating member 46 is shown to be constructed in the form of a bracket for retaining each of electrode members 42, 44. Transverse plate 56 of bracket 46 defines a pair of apertures 58 to permit connection between the respective conductors 48, 50, and their connected electrode members 42, 44 when mounted on bracket 46.

Turning to FIGS. 7 and 8, another embodiment of this invention is shown, in the form of the distal end of lead 10c, which may be identical in construction and function to the leads of the previous drawings except as otherwise shown. Lead 10c, carrying out insulation 60 along most of its length, carries at its distal end a hemispherical electrode member made of three separate, electrically isolated electrode members 62, 63, 64. Electrode members 62–64 may be carried by an insulating bracket 66, which may be similar construction and material to insulating bracket 46 except that a branched insulating wall 68 is provided so that the three electrode members may be placed in close proximity to each other, occupying a common longitudinal area on the lead, while being electrically insulated from each other. Appropriate electrical conductors similar in function to conductors 48, 50 extend, respectively, from each of electrode members 62–64 rearwardly through the interior of lead 10c to be terminated in conventional manner for communication with pacer electronics or the like.

Thus, a hemispherical electrode may be subdivided into three independently operating electrode members, for advantageous use in the manner previously described.

FIGS. 9 and 10 disclose another embodiment, in which the distal end of lead 10d carries a pair of opposed electrode segments 70, 72, which are embedded in the insulating material 74 that forms lead 10d, so that a separate insulating bracket member is not required. The electrode segments may, for example, be positioned in a mold, with insulating material such as polyurethane or silicone rubber being formed around the spaced electrodes as part of a molding process for the lead. As before, appropriate conductors communicate with electrode members 70, 72 to provide separate, electrically insulating electrical communication with a connector at a proximal portion of the lead, for connection with a switching and electronics system for use of the lead.

The above has been offered for illustrative purposes only, and is not intended to limit the scope of the invention of this application, which is as defined in the claims below.

That which is claimed is:

1. A method for cardiac pacing and sensing, which comprises the steps of:
   providing a cardiac pacing lead having a distal tip at one end thereof, a first electrode positioned at said distal tip and a second electrode positoned at said distal tip, with said first and second electrodes being separate from each other, transversely spaced from each other, and electrically isolated from each other;
   providing a first electrical conductor for said first electrode;
   providing a second electrical conductor for said second electrode, said second electrical conductor being a different electrical conductor from said first electrical conductor;
   inserting said lead into a heart chamber;
   combining said first and second electrodes via said first and second electrical conductors to provide a relatively large surface electrode area for sensing cardiac activity; and
   using only said first electrode for providing pacing pulses to the heart chamber, said first electrode having a relatively smaller surface electrode area than said relatively large surface area used for sensing and resulting from the combination of said first and second electrodes.

* * * * *